United States Patent [19]
Horn et al.

[11] Patent Number: 5,888,481
[45] Date of Patent: Mar. 30, 1999

[54] CINNAMAMIDES AND THEIR USE AS STABILIZERS

[75] Inventors: Keith A. Horn, Long Valley; Richard B. Heath, Morristown; David B. Schwind, Blairstown, all of N.J.

[73] Assignee: AlliedSignal Inc., Morris Township, N.J.

[21] Appl. No.: 536,919

[22] Filed: Sep. 29, 1995

[51] Int. Cl.[6] .......................... A61K 7/42; C07C 255/00; C07C 233/00
[52] U.S. Cl. .............................. 424/59; 424/60; 558/388; 558/389; 558/390; 558/393; 558/401; 558/404; 564/155; 564/156; 564/161
[58] Field of Search ........................ 424/59, 60; 564/155, 564/156, 161; 558/388, 389, 390, 392, 393, 401, 404

[56] References Cited

U.S. PATENT DOCUMENTS

| | | |
|---|---|---|
| 3,077,403 | 2/1963 | Trucker . |
| 3,174,937 | 3/1965 | Strobel et al. . |
| 3,272,855 | 9/1966 | Strobel et al. . |
| 3,775,477 | 11/1973 | Diana . |
| 4,062,934 | 12/1977 | Tilly et al. . |
| 4,165,319 | 8/1979 | von der Crone et al. . |
| 4,883,653 | 11/1989 | Raynor . |
| 5,200,528 | 4/1993 | Wooden et al. . |
| 5,272,175 | 12/1993 | Hansen, Jr. et al. . |
| 5,342,955 | 8/1994 | Wooden et al. . |
| 5,382,595 | 1/1995 | Minami et al. . |

*Primary Examiner*—Johann Richter
*Assistant Examiner*—Joseph Murray
*Attorney, Agent, or Firm*—John A. Squires; Colleen D. Szuch

[57] ABSTRACT

The invention relates to novel cinnamamides, a process for their manufacture and their use as UV absorbers. The cinnamamides of the invention may be used as UV absorbers in a variety of engineered resins such as polyamides (especially nylon 6 and 6,6), polycarbonates, polyacetals, polysulfones, polyimides, polyaryletherketones, and polyesters, (especially PET and PBT), as well as, other polymers such as polyvinylchloride and polyolefins (polyethylenes and polypropylenes).

38 Claims, No Drawings

5,888,481

CINNAMAMIDES AND THEIR USE AS STABILIZERS

BACKGROUND OF THE INVENTION

The invention relates to a novel class of cinnamamides, a process for their manufacture and their use as ultraviolet (UV) stabilizers. Ultraviolet light (wavelengths between 280 nm and 400 nm) is known to degrade exposed organic matter. Materials used in exterior applications as well as interior applications (where there is exposure to UV rays through glass) such as fibers and fabrics [for use in applications including marine sails and ropes, awnings, tents, flags, upholstery (including interior automotive fabrics), carpet, sports equipment, soft-sided luggage, seatbelt webbing, animal control webbing and clothing], molded plastic parts [for use in applications including automobile parts (such as mirror housings, door handles, body panels and bumpers), as well as, sports equipment and tool housings], plastic films [for applications including agricultural applications (such as greenhouse coverings, crop protection and food packaging), and packaging for chemical products (such as pesticides and fertilizers)], and plastic coatings [for applications including paint] are susceptible to photochemical degradation.

Specifically, polymers develop undesirable color or haze and subsequently lose their transparency and physical properties such as tensile strength, flexibility, gloss and impact resistance. Dyed, pigmented and mineral and glass filled plastics and textiles (e.g., carpet fibers) and color containing plastics [e.g. aliphatic and aromatic polyamides including nylon 6 and nylon 6,6; polycarbonate; polyesters such as poly(ethyleneterephthalate) (PET) and poly (butyleneterephthalate) (PBT); polyolefins such as poly (ethylene), poly(propylene); aramids; acrylates; acetates; polyvinylchloride; polyimides; fluoropolymers; polyurethanes; polyacetals; polysulfones and polyaryletherketones] fade, become brittle, lose their elasticity and eventually completely deteriorate.

As a result, the plastics industry has developed a broad range of stabilizers to prevent UV degradation. These include, radical scavengers such as hindered amine light stabilizers (HALS), phosphites and phenolic antioxidants (AOs), thioethers, metal dithiolates, sulfoxides, among others and ultraviolet light absorbers such as benzotriazoles (BZTs), hydroxybenzophenones (HBPs), cinnamates, benzylidene malonates and nickel chelates. A broad review of these and other stabilizers can be found in J. F. Rabek, "Photostabilization of Polymers; Principles and Applications", Elsevier Applied Science, NY, 1990.

In addition to protecting against the damaging effects of UV light in the plastic itself, UV absorbing stabilizers can be used in transparent packaging to absorb UV light and thereby prevent damage to the package contents (such as food where light induced oxidation can occur in natural oils leading to undesirable odors and rancidity or drugs).

In order to be useful in plastics applications, a candidate UV light absorber must have a strong UV light absorptivity at wavelengths between 280 and 400 nm, be colorless, photostable, nonvolatile under processing and end use conditions, chemically inert during storage, processing and application conditions, and have an efficient mechanism for the conversion of light energy to heat without initiating radical or other degradation processes. Low volatility, chemical inertness, and thermal stability are particularly important considerations for the "engineering plastics" such as polyesters, polyamides, polycarbonates, polyacetals, polysulfones, polyimides, and polyaryletherketones where melt processing conditions often reach or exceed temperatures of 300° C. with lengthy melt residence times. Few of the commercially available UV stabilizers can withstand these processing conditions for reasons discussed below.

The two dominant classes of commercially available UV absorbers are benzotriazoles (BZTs) and hydroxybenzophenones (HBPs). Both utilize an excited state intramolecular proton transfer from a hydroxyl group to dissipate light energy following absorption of ultraviolet light. Neither is without problems. The requisite hydroxyl groups of both the BZTs and the HBPs often result in severe color formation, especially in pigmented and filled plastics such as glass and mineral filled polyamides or polyesters. Often the color formation is a result of complexation with pigments, colorants, catalysts or fillers. In basic media, deprotonation of the phenolic hydroxyl groups of these compounds results in formation of strong yellow colors. Additionally, in hydrogen bonding plastics such as polyamides, the hydroxyl group is tied up via hydrogen bonding with the polymeric substrate which decreases the absorption strength of the stabilizer and narrows the absorption band, thus reducing the effective wavelength for the stabilizer and eliminating the mechanism for excited state energy dissipation.

In addition, many of the commercially available benzotriazoles are too expensive (at the typical required loadings in plastics) and/or volatile, and fume during processing. The lower volatility, higher molecular weight BZT dimers are costly and those that are connected via ester linkages can cause loss of molecular weight during melt processing of polyesters as a result of ester—ester interchange reactions.

For applications in which plastics are exposed to wavelengths below 320 nm, the BZTs are less effective because their absorption strength drops off below 315 nm, a critical absorption region for undyed polyester and polycarbonate stabilization. HBPs which absorb strongly in the general region of 340–360 nm also have a lower absorption strength in the general region of 290 to 330 nm. Many commercial HBPs are also too volatile for processing in many high temperature engineering resins and cause yellowing in polyesters. Finally, many commercial HBPs cause chain scission thereby degrading the molecular weight of polyesters such as PET and PBT during processing (e.g. spinning).

Two other general classes of absorbers are sold commercially. These are the oxanilides and cinnamates (esters of cinnamic acid). The oxanilides are thought to dissipate UV light energy by an intramolecular excited state proton transfer from an amide nitrogen to an amide carbonyl. These absorbers therefore can potentially be rendered ineffective by hydrogen bonding with the polymer resin in e.g. polyamides. The absorption strength of oxanilides is also somewhat low compared to other UV absorbers. The cinnamates (used as sunscreens) do not suffer from these same drawbacks since they have high absorption strengths and dissipate excited state energy through cis-trans isomerization of the cinnamate double bond (and therefore cannot readily be rendered ineffective by hydrogen bonding polymers). However, these materials are generally either too volatile to withstand processing at 250–315° C. or they are oily liquids which cause lubrication in processing equipment (e.g. screw lubrication in extruders) and phase separation.

Ester—ester interchange is a problem for the monomeric cinnamates and prevents them from being used in melt-processed polyester objects such as fibers since the molecular weight of the polyester polymer is drastically reduced. In melt extruded polyamides, the basic cinnamate chromophore is destroyed, by a mechanism that most likely involves nucleophilic attack at the β-position of the unsaturated cinnamate ester. It is also well known that cinnamates can undergo various photochemically induced cyclization reactions of which 2+2 photodimerization is a prime example. The dimerization destroys the chromophore necessary for UV stabilization.

Various cinnamamides have been used in the art as UV stabilizers for engineering resins. See U.S. Pat. Nos. 3,174,937 ('937 patent) and 3,272,855 ('855 patent) to General Aniline & Film Corporation and U.S. Pat. No. 4,883,653 ('653 patent) to Olin Corporation. The cinnamic acid amide dimers of the '653 patent have only hydrogen substitution in the α and β positions. Thus, these molecules are susceptible to chromophore destruction via both nucleophilic conjugate addition and 2+2 photodimerization. The same is true of the cinnamic acid dimers disclosed in the '937 patent. The alkoxy substitution (RO) present in the compounds disclosed in the '855 patent yields base absorption maxima at ca. 335 nm, well into the UV-A region. Since the $X_1$ substituents in the '855 patent are chosen to cause bathochromic (red shifts) or auxochromic (red shift and increased absorption strength), these materials are unable to effectively block UV-B wavelengths in contrast to the molecules of the present invention.

The compounds disclosed in the '937 patent suffer both from β-hydrogen substitution, making them susceptible to nucleophilic conjugate addition during processing and from an inability to effectively block the UV-B region (methoxy substituted naphthyl chromophore).

The unique bis-[α,β-disubstituted cinnamic acid amides] (cinnamamides) of the invention are useful as stabilizers for engineering resins and other polymers which are processed at high temperatures (typically above 200° C., most typically above 250° C. and specifically from 275°–325° C.). Unlike the commercially available stabilizers, these cinnamamides have high UV absorption strength (including the UV-B range around 295 nm, a critically important portion of the action spectrum for engineered resins such as undyed polyesters and polycarbonates), low volatility, are thermally and chemically stable, do not undergo ester-ester interchange, and utilize a cis-trans photoisomerization as a light dissipation mechanism that does not involve an intramolecular proton transfer. The cinnamamides of the invention are sterically blocked via substitution in the β position to prevent reactivity with nucleophilic end groups and additives, especially bases, found in the plastics being stabilized. The steric hindrance by functional groups attached to such a stabilizer double bond would also serve to prevent photodimerization.

DESCRIPTION OF THE INVENTION

Specifically, our invention is directed to bis-[α,β-disubstituted cinnamic acid amides] of the structure:

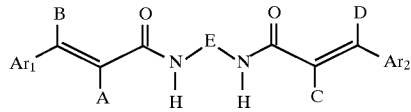

wherein:
  $Ar_1$ and $Ar_2$ are the same or different and are selected from the group consisting of phenyl, heterocyclicaromatic, annelated phenyl and annelated heterocyclicaromatic radicals and may be substituted in any position with the same or different group(s);

B and D are the same or different organic radicals but neither is hydrogen;

A and C are the same or different organic radical; and

E is a divalent or trivalent organic radical with one of the following provisos:
    excluding compounds (including isomers thereof) wherein: $Ar_1$ and $Ar_2$ are the same and are phenyl and are substituted with —OR wherein R is hydrogen or an organic radical, A and C are the same and are cyano, B and D are the same and are alkyl or alkenyl of 1–35 carbon atoms and E is a divalent organic radical; except when such compounds are used in combination with other compounds of said formula which do not have this excluded structure;
    provided that when A and C are the same and are cyano, B and D are the same and are alkyl or alkenyl of 1–30 carbon atoms, E is a divalent radical and $Ar_1$ and $Ar_2$ are the same and are phenyl, $Ar_1$ and $Ar_2$ are not both substituted with —OR wherein R is hydrogen or an organic radical; except when such compounds are used in combination with other compounds of said formula which do not have this excluded structure;
    provided that when A and C are the same and are cyano, B and D are the same and are alkyl or alkenyl of 1–30 carbon atoms, E is a divalent radical and $Ar_1$ and $Ar_2$ are the same and are phenyl, neither $Ar_1$ nor $Ar_2$ is substituted with —OR wherein R is hydrogen or an organic radical; except when such compounds are used in combination with other compounds of said formula which do not have this excluded structure;
    provided that when A and C are the same and are cyano, B and D are the same and are alkyl or alkenyl of 1–30 carbon atoms, E is a divalent radical and $Ar_1$ and $Ar_2$ are the same and are phenyl, none of $Ar_1$, $Ar_2$ B and D are substituted with —OR; except when such compounds are used in combination with other compounds of said formula which do not have this excluded structure;

Where double bond configurational isomers are possible, any of the E or Z (cis and trans) isomer combinations are acceptable and all are implied by the structures drawn herein, although only single isomers are drawn for clarity.

Suitable groups for $Ar_1$ and $Ar_2$ include phenyl or heterocyclicaromatic radicals including 2-, 3-, or 4-pyridyl or annelated phenyl or annelated heterocyclicaromatic radicals including quinolinyl or isoquinolinyl, 1- or 2-naphthyl, pyrenyl and other polycyclic aromatics and may be substituted in any position with the same or different group(s) including substituted and unsubstituted straight-chain and branched alkyl of from 1 to ca 25 carbon atoms including cyanoalkyl, alkoxyalkyl, partially or fully substituted haloalkyl including fluorinated or chlorinated alkyl, (e.g. chloromethyl or trifluoromethyl), amino alkyl such as mono or dialkylaminoalkyl, silylalkyl including trialkylsilylalkyl; substituted or unsubstituted straight chain and branched alkenyl of from 2 to ca 25 carbon atoms such as vinyl, allyl, methallyl, —$CH_2C_nH_{2n-1}$, crotyl, but-2-enyl, but-3-enyl, 2-methylpropenyl, pent-2-(or 3- or 4- or 5-)enyl, hex-2-enyl, dec-2-enyl; and wherein when said alkenyl is substitued, it may be substituted with groups including cyano, alkoxy, amino, silyl and halogen; nitro; halogen such as fluoro, chloro, or bromo; thioethers; alkyl or arylsulfone; sulfonic ester; —$CH(OCH_3)_2$ and —$CH(OCH_2CH_3)_2$ ;cyclic ketal or acetal including

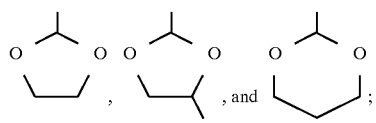
, and ;

phenyl or substituted phenyl, including multiply- substituted phenyls; biphenyl, or substituted biphenyl; pyridyl including 2-, 3-, or 4-pyridyl; a heterocyclic aromatics; and —OR where R is hydrogen or any substituted or unsubstituted organic radical.

Preferably, $Ar_1$ and $Ar_2$ are selected from the following groups: phenyl or substituted phenyl; 1- or 2-naphthyl; and 2-, 3- or 4- pyridyl. In a more preferred embodiment, $Ar_1$ and $Ar_2$ are phenyl or substituted phenyl.

Suitable groups for B and D include substituted or unsubstituted straight and branched chain alkyl, of from 1 to ca 25 carbon atoms including cyanoalkyl, alkoxyalkyl, haloalkyl such as partially fluorinated or chlorinated alkyl, aminoalkyl such as mono or dialkylaminoalkyl, and silylalkyl including trialkylsilylalkyl; substituted or unsubstituted straight chain or branched alkenyl of from 3 to ca 25 carbon atoms such as allyl, methallyl, —$CH_2C_nH_{2n-1}$, crotyl, but-2-enyl, but-3-enyl, 2-methylpropenyl, pent-2 (or 3- or 4- or 5-)enyl, hex-2-enyl, dec-2-enyl; and wherein suitable groups for substitution include cyano, alkoxy, halo, amino and silyl; phenyl, substituted phenyl including alkyl-substituted phenyl such as tolyl, or xylyl, thioether substituted phenyl including 4-propylthiophenyl and 4-phenylthiophenyl; —OR substituted phenyl, wherein R is hydrogen or any organic radical, including alkoxy-substituted phenyl such as 4-methoxyphenyl, alkenyl-substituted phenyls including 4-vinylphenyl; cyano-substituted phenyl including 4-cyanophenyl; nitro substituted phenyl such as 4-nitrophenyl; halo-substituted phenyl such as 2- or 4-chloro-, bromo- or fluorophenyl; haloalkyl such as chloromethyl- or trifluoromethyl-substituted phenyl; alkyl or arylsulfone-substituted phenyl such as 4-methylsufonylphenyl; sulfonic ester-substituted phenyl; —$CH(OCH_3)_2$ and —$CH(OCH_2CH_3)_2$ substituted phenyl; cyclic ketal or acetal- including

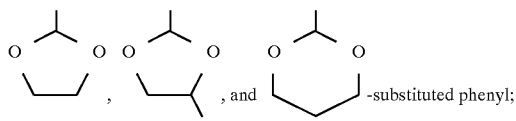
, and -substituted phenyl;

multiply substituted phenyls having any of the substitutents listed above; substituted or unsubstituted polycyclic aromatics and heterocyclic aromatics such as biphenyl, pyridyl including 2-, 3-, or 4-pyridyl; quinolinyl or isoquinolinyl, 1- or 2-naphthyl, pyrenyl but neither may be hydrogen.

Preferably, B and D are chosen such that they have sufficient steric bulk to prevent both nucleophilic attack at the position β to the carbonyl and 2+2 photodimerization. Suitable steric bulk can be achieved using branched chain alkyl, phenyl, substituted phenyl, pyridyl, substituted pyridyl and annelated phenyl or heterocyclicaromatics. Phenyl, substituted phenyl and pyridyl groups are preferred on a cost-performance basis. In a preferred embodiment, B and D are selected from the following: phenyl, substituted phenyl, pyridyl and substituted pyridyl. In a still more preferred embodiment, B and D are phenyl or pyridyl.

Suitable groups for A and C include cyano, ester (—$CO_2R$) wherein R may be any compatible substituted or unsubstituted organic radical such as a straight chain or branched aliphatic hydrocarbon or aromatic group having from 1 to 20 carbon atoms, and amide (CONHR) wherein R may be hydrogen or any compatible substituted or unsubstituted organic radical such as a straight-chain or branched aliphatic or aromatic group having from 1 to 20 carbon atoms. Preferably, A and C are selected from cyano and amide. In a more preferred embodiment, A and C are cyano.

Suitable groups for E include divalent radicals selected from among substituted or unsubstituted straight or branched-chain aliphatics of from 2 to ca. 20 carbon atoms, including ethanediyl, 1,2-propanediyl, 1,3-propanediyl, 2-methyl-1,2-propanediyl, 1,4-butanediyl, 1,4-cyclohexanediyl, 1,5-pentanediyl, 1,6-hexamethylenediyl, 1,8-octanediyl, 1,9-nonanediyl, 1,8-menthanediyl, and wherein suitable groups for substitution include cyano, alkoxy, halo, amino and silyl; substituted or unsubstituted straight or branched-chain alkenyl of from 2 to ca 25 carbon atoms including 1,2-maleonitrilediyl; and 1,2-fumaronitrilediyl; aromatic or heterocyclic aromatic connecting groups including 2,3-toluenediyl, 2,4-toluenediyl, 2,5-toluenediyl, 2,6-toluenediyl, 3,4-toluenediyl, p-xylylenediyl, m-xylylenediyl, 4,4'-biphenyldiyl, 1,4-, 2,3-, and 1,8-naphthalenediyl, 2,4-pyridinediyl, 2,3-pyridinediyl, 2,6-pyridinediyl, 2,4-pyrimidinediyl, 1,2,4-triazole-3,5-diyl, 4,5-dimethyl- 1,2-phenylenediyl, 4,4'-octafluorobiphenyldiyl and other fluorinated aromatics; siloxane or polysiloxane containing diyls of structure —R'—O(Si(R)$_2$O)n—R'— where R and R' are comprised of straight-chain or branched alkyl or aromatic radicals of from 1 to ca. 20 carbon atoms; ether or polyether containing diyls of the structure —R'—O(RO)n—R' where R and R' are comprised of straight-chain or branched alkyl or aromatic radicals of from 1 to ca. 20 carbon atoms. Siloxanes and partially or fully fluorinated alkyl, alkenyl and aryl connecting groups obtained from the corresponding diamines are also acceptable. Organic diyls derived from straight chain aliphatic linking groups including —(CH$_2$)$_6$— as well as aromatics such as m-xylylenediyl and 2,4-toluenediyl are preferred. Aliphatic and aromatic linking groups derived from triamines such as melamine are also acceptable as described in the structure shown below.

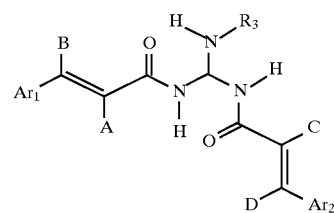

$R_3$ can be any organic radical including those described for B and D by selecting different groups one can modify the physical properties such as solubility and (dispersability), or chemical reactivity (for attachment to other molecules, substrates, polymers and other compositions). Preferred groups for $R_3$ substituted or unsubstituted straight chain or branched alkyl of from 1 to ca. 25 carbon atoms wherein when said alkyl is substituted, it is substituted with a group selected from the group consisting of cyano, alkoxy, halo, amino and silyl; unsubstituted or substituted straight chain or branched alkenyl of from 2 to ca. 25 carbon atoms wherein when said alkenyl is substituted, it is substituted with a group selected from the group consisting of cyano, alkoxy, halo, amino and silyl; cyano; nitro; halo; thioether; alkyl or arylsulfone; sulfonic ester; acetal, cyclic acetal; ketal, cyclic ketal; phenyl, substituted phenyl, multiply substituted phenyls wherein said phenyls may be substituted with any of the groups listed above; biphenyl, substituted biphenyl; pyridyl, substituted pyridyl and heterocyclicaromatics; and —OR where R is hydrogen or any organic radical; and ethers or polyethers of the structure —R'O(RO)n—R" wherein R, R' and R" are substituted or unsubstituted straight chain or branched chain alkyl or aromatic radicals of from 1 to ca. 20 carbon atoms. More preferred embodiments are substituted and unsubstituted straight or branched chain alkyl or aromatic radicals and cinnammoyl groups. A most preferred embodiment would be one in which $R_3$ is an α,β-disubstituted cinnamoyl group,

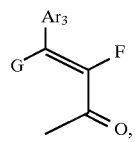

as in the structure shown below.

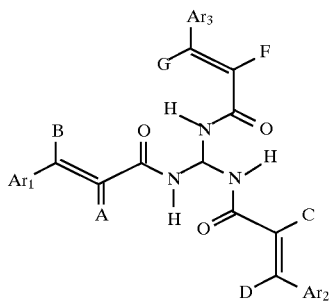

In these compositions, F can be any of the organic radicals assigned to A or C, and G can be any of the organic radicals assigned to B or D. $Ar_3$ may be the same or different from $Ar_1$ and $Ar_2$ and can be any of the substituted or unsubstituted phenyl or heterocyclicaromatic radicals or annelated phenyl or annelated heterocyclicaromatic radicals assigned to $Ar_1$ and $Ar_2$ and can be substituted in any position with the same group or groups identified for substitution on $Ar_1$ or $Ar_2$. When E is a trivalent radical, preferably it is selected from among (—CH$_2$CH$_2$)$_3$N and 2,4,6-melaminetriyl. In a more preferred embodiment, E is 2,4,6-melaminetriyl.

Preferred cinnamamides of the invention include:

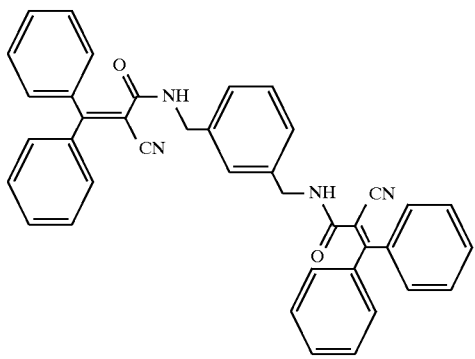

CAmX

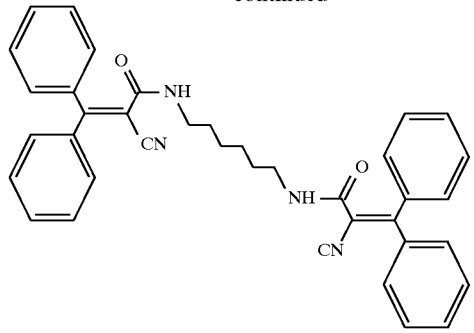

CAHM

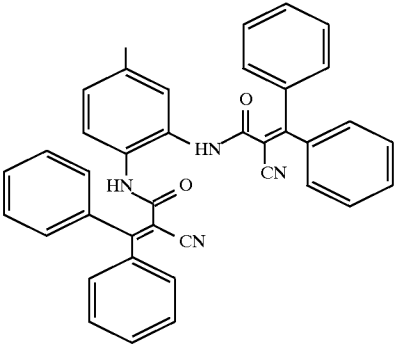

CAmpT

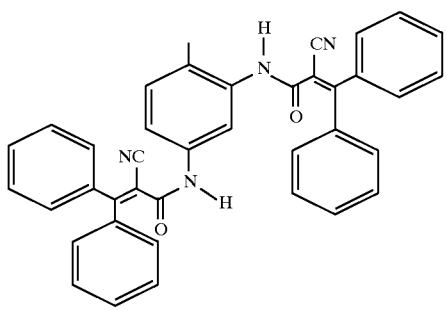

CAopT

When the cinnamamides of the invention are utilized as UV absorbers, their substituents must be chosen such that they do not cause a bathochromic (red) shift of the absorption band into the visible spectral region and so that they are photochemically stable. Substitution of $Ar_1$ and $Ar_2$ in the 2- and 4-positions with strongly electron donating groups such as dialkylamino are generally to be avoided in stabilizer applications since they can shift the absorption band into the visible region, thus creating a colored material.

The cinnamamides of the invention are useful as UV stabilizers for poly(vinylchloride)(PVC), polyolefins such as polyethylene and polypropylene and especially for engineering plastics including, polyesters, polyamides, polycarbonates, polyacetals, polysulfones and polyaryletherketones. The composition of and method for preparing formulations containing these stabilizers and engineering plastics will depend on the resin selected and the application in which the formulation will be used (e.g., food packaging, carpet fibers, automobile parts). Such formulations and methods are well known in the art. See, for example, US Pat. Nos. 4,174,358, 5,391,640, 5,079,339, 5,055,355, 5,206,309, 4,362,585, 4,427,825, 5,139,878 and 4,175,147 all of which are incorporated herein by reference. For use in high temperature engineering resins the groups of the cinnamaides must be selected such that they are sufficiently thermally stable to be utilized in high temperature processing. The selection of such groups will readily occur to one skilled in the art.

The compounds of the current invention would generally be used in engineering plastics that are processed at temperatures above ca. 250° C. at typical loadings of from about 0.05 to about 10 wt % (depending upon solubility and the extent of fillers, plasticizers and other property modifiers in the plastic), more typically at loadings of about 0.1 to about 2 wt % and most typically from about 0.5 to about 1.5 wt %.

The cinnamamide dimers of the present invention can also be utilized in sunscreen formulations which typically include a combination of UV-A and UV-B absorbing compounds to absorb most of the skin damaging light between 280 and 400nm. The cinnamamides can be dissolved or dispersed in a cosmetically acceptable base known to one well versed in the art. If the cinnamamide dimer chosen is not soluble, it can be rendered dispersible via 3-roll milling and using a cosmetic oil, or other dispersing aid. Preferred concentrations in sunscreen lotions and oils would be between 1 and 50 wt %. More preferred concentrations would be between 5 and 25 wt %.

The preferred cinnamides listed above provide coverage in the UV-B (280 nm–315 nm) spectral region. If coverage in the UV-A (315 nm–400 nm) spectral region is desired, substitution of $Ar_1$, $Ar_2$, , B or D should include one or more electron donating substituents such as RS—, $H_2N$— or HRN—, which will cause a bathochromic (red) shift of the absorption maximum.

By using only individual standard UV absorbers one can cover only specific spectral regions based on the inherent absorption properties of the functional groups present in the molecule (e.g. benzotriazole). The novel cinnamamides of the invention may be used in combination (typically two or three) with themselves or with other commercially available stabilizers to provide absorption maxima at different locations within the UV-B and UV-A spectral regions. If, for example, one wanted protection over the entire UV-B and UV-A region, three cinnamamides with absorption maxima at ca. 295 nm, 325 nm and 350 nm could be selected. Variation of substituent patterns in $Ar_1$, $Ar_2$, B or D can readily generate such a complementary set. Such a set of absorbers, all having similar chemical, physical and photochemical properties, could be effectively combined in varying ratios to produce the optimal absorbance for coverage of a given plastic, fabric or part based on its action spectrum for degradation. The selection of cinnamamides (including with other commercially available stabilizers) and proportions of each will readily occur to those skilled in the art. Typically, the cinnamamides of the invention would be used at loadings of about 0.1 to about 5 wt % with about 0.1 to about 5 total wt % of the other stabilizers. More typically, the cinnnamamides would be used at about 0.1 to about 2 wt % with about 0.1 to about 2 total wt % of the coadditives. Most typically, the cinnnamamides would be used at about 0.1 to about 1 wt % with about 0.1 to about 1 total wt % of the coadditives.

Unsymmetrical cinnamamides of the current invention with substituents on either $Ar_1$ and B or $Ar_2$ and D that shift the absorption maximum of one of the cinnamic acid moieties to longer wavelength would cover both the UV-B and portions of the UV-A regions. These materials would show significant advantage over the prior art.

Suitable other commercially available stabilizers with which the novel cinnamamides of the invention may be combined include, radical scavengers such as hindered amine light stabilizers (HALS), phosphites and phenolic antioxidants (AOs), thioethers, metal dithiolates, sulfoxides, among others and ultraviolet light absorbers such as benzotriazoles (BZTs), hydroxybenzophenones (HBPs), cinnamates, benzylidene malonates, nickel chelates, oxanilides and copper-based heat stabilizers or combinations and permutations thereof Any combination creating significant color changes would of course be avoided. Other stabilizers which can be used in combination with the novel cinnamamide UV light absorbers of the current invention can be found in the book by J. F. Rabek, "Photostabilization of Polymers; Principles and Applications", Elsevier Applied Science, NY, 1990.

The cinnamamides of the invention are not commercially available. They may generally be prepared in high-yield via a Knoevenagle condensation of a substituted benzophenone with a suitable ester (substituted in the $\alpha$-position with an electron withdrawing group such as cyano), followed by hydrolysis of the resulting $\alpha,\beta$-disubstituted cinnamate to the corresponding cinnamic acid, further transformation to the acid chloride using thionyl chloride or other chlorinating agent, and finally reaction of the substituted cinnamoyl chloride with a suitable diamine or triamine. This synthetic route is explicitly described in Examples 1 and 2 below. Other synthetic routes will readily occur to those skilled in the art.

EXAMPLE 1 m-Xylylenediamine-N,N'-bis(2-cyano-3,3-diphenylpropenamide) [CAMX]

Synthesis: A solution of m-xylylene diamine (2.6 g, 0.019 mol) in methylene chloride (10 mL) was added to a stirred solution of 2-cyano-3,3-diphenyl-2-propenoyl chloride (10.4 g, 0.039 mol) in methylene chloride (54 mL) under a nitrogen flux and stirred for 1 hour. Triethylamine (3.97 g, 0.039 mol) was then added and the mixture stirred for 18 hours. The solvent was removed and the white product was dissolved in hot acetonitrile (300 mL) and filtered to remove insoluble material. Upon cooling a fine, off-white precipitate was formed. A second recrystallization from acetonitrile afforded white material with a melting point of 227°–228° C. A yield of 6.7 g, 67% of theory, of m-xylylenediamine-N, N'-bis(2-cyano-3,3-diphenyl-propenamide) was obtained. Mass spectrometry and $^1$H NMR confirmed the structure of the product.

EXAMPLE 2

3,4-Diaminotoluene-N,N'-bis(2-cyano-3,3-diphenylpropenamide) [CAmpT]

Synthesis: A solution of 3,4-diaminotoluene (3.05 g, 0.025 mol) in methylene chloride (12 mL) was added to a stirred solution of 2-cyano-3,3-diphenyl-2-propenoyl chloride (13.9 g, 0.05 mol) in methylene chloride (100 ML) under a nitrogen flux. Methylene chloride was added to the reaction mixture to bring the total volume up to 250 mL of solvent and the solution was extracted with water (100 mL). The organics were recovered and concentrated to give a crude yield of 15.0 g. A portion (2.0 g) of the crude material was further purified by dissolution in hot ethylacetate (40 mL) followed by the addition of hexanes (20 mL) and cooling to yield 1.0 g of a fine white precipitate which had a melting point of 257°–259° C. The structure of the product 3,4-Diaminotoluene-N,N'-bis(2-cyano-3,3-diphenyl-propenamide) was confirmed by mass spectrometry and $^1$H NMR.

EXAMPLE 3

1,6-Diaminohexane-N,N'-bis(2-cyano-3,3-diphenylpropenamide) [CAHM]

Synthesis: A solution of hexamethylene diamine (65.11 g, 0.56 mol) in methylene chloride (125 mL) was added to a solution of 2-cyano-3,3-diphenyl-2-propenoyl chloride (300 g, 1.12 mol) in methylene chloride (3 L) over a period of one hour. The reaction mixture was stirred for an additional four hours whereupon triethylamine (113.40 g, 1.12 mol) was added in a dropwise manner. The reaction was stirred for two days and filtered. The precipitate was rinsed three times with methylene chloride (1.5 L) to remove the residual yellow color. The precipitate was then added cautiously to two liters of hot water and stirred at a boil for approximately 45 minutes. The solid was filtered and rinsed with two additional liters of hot water. The solid was stirred for approximately 40 minutes with hot acetone and filtered. The white solid was dried in a vacuum oven at 60° C. to remove residual acetone affording 289.15 g of the product 1,6-diaminohexane-N,N'-bis(2-cyano-3,3-diphenylpropenamide) (89% of theoretical), with a melting point of 235°–238° C. $^1$H NMR confirmed the structure.

EXAMPLE 4

2,4-Diaminotoluene-N,N'-bis(2-cyano-3,3-diphenylpropenamide) [CAopT]

Synthesis: 2,4-Diaminotoluene (37.25 g, 304 mmol) was added in equal portions to a solution of 2-cyano-3,3-diphenyl-2-propenoyl chloride (167.33 g 625.0 mmol) in chloroform (400 mL) which was cooled to 0° C. A solution of N,N-dimethylaminopyridine (3.73 g, 30.5 mmol) in chloroform (75 mL) was added to this mixture in a dropwise manner. The reaction was heated at reflux for three hours then cooled and triethylamine (64.79 g, 640.3 mmol) was added in a dropwise manner. The reaction was then eated at reflux overnight. After cooling, the reaction mixture was sequentially extracted with water, 1N HCl, 10% $KCO_3$ and finally water. The organic layer was dried with magnesium sulfate and concentrated in vacuo. The solid obtained in this manner was dried under vacuum and recrystallized from 190 proof ethanol. The white solid was dried in a vacuum oven at 60° C., to remove residual ethanol, to give 128.00 g of the product 2,4-diaminotoluene-N,N'-bis(2-cyano-3,3-diphenylpropenamide) (71% of theoretical), with a melting point of 139°–141° C. $^1$H NMR confirmed the structure.

EXAMPLE 5

4,4'-Diaminooctafluorobiphenyl-N,N'-bis(2-cyano-3,3-diphenylpropenamide)

[CAFBP] Synthesis: A solution of 4,4'-diaminooctafluorobiphenyl (4.9 g, 0.015 mol) in 50% diethyl ether:methylene chloride (100 mL) is added in a dropwise manner to a solution of 2-cyano-3,3-diphenyl-2-propenoyl chloride (8.7 g, 0.032 mol) in 50% diethyl ether-:methylene chloride (75 mL) which is cooled to 0° C. A solution of N,N-dimethylaminopyridine (0.18 g, 0.0015 mol) in methylene chloride (4.0 mL) is added to this mixture in a dropwise manner. The reaction is heated at reflux for three hours then cooled and triethylamine (3.24 g, 0.032 mol) is added in a dropwise manner. Reflux is then continued overnight. After cooling, the solvent is removed in vacuo. The crude solid is suspended in water (100 mL) and stirred at a boil for 20 minutes. The solid is removed by filtration and dried. The product is further purified by recrystalization. The solid is dried in vacuo to give the product 4,4'-diaminooctafluorobiphenyl-N,N'-bis(2-cyano-3,3-diphenylpropenamide).

EXAMPLE 6

This example was designed to determine whether the cinnamamides of the invention (samples 1–12) can withstand high temperature processing. The cinnamamides listed in Table 1 below were dry blended with AlliedSignal's commercially available 8207F Nylon 6 resin at loadings of 1.0 or 0.5 wt %. The composition was extruded on a Haake TW-100 twin screw extruder equipped with conical feed screws and a mixing element. The polymer melt was maintained at 273° C. and the barrel sections were heated to 215°, 235°, and 240° C. respectively. The extruder screws were maintained at 50 RPM which resulted in a torque of approximately 1400. The polymer melt was formed into film using a 6" film die maintained at 240° C. with a die gap of 0.021" to give film with a nominal thickness of 0.0017 cm.

The amount of additive in the film was calculated using Beer's Law and is represented as a percent of the concentration that would have been obtained had all of the additive survived the processing conditions. All UV/Vis spectra were obtained on a Cary 5E spectrophotometer. Extinction coefficients were measured in either methylene chloride or DMF acetonitrile solution. Film thicknesses were measured in a minimum of 5 places using a Mitutoyo 293 digimatic micrometer. The average of the readings was used to calculate the concentration of additive in the film. The results are reported in Table 1 below.

TABLE 1

Comparison of the absorbance of β-phenyl substituted cinnamamide dimers and β-unsubstituted cinnamamide dimers following processing in Nylon 6 films.

| Sample # | Additive | Dust on Loading (wt. %) | Content in Film (% of Loading) |
| --- | --- | --- | --- |
| 1 | CAmX | 0.5 | 74 |
| 2 | CAmX | 0.5 | 65 |
| 3 | CAmX | 0.5 | 76 |
| 4 | CAmX | 1.0 | 87 |
| 5 | CAmX | 1.0 | 84 |
| 6 | CAmX | 1.0 | 74 |
| 7 | CAHM | 0.5 | 95 |
| 8 | CAHM | 0.5 | 89 |
| 9 | CAHM | 0.5 | 80 |
| 10 | CAHM | 1.0 | 92 |
| 11 | CAHM | 1.0 | 77 |
| 12 | CAHM | 1.0 | 87 |
| 13 | bis-MECCA* | 0.5 | 41 |
| 14 | bis-MECCA | 0.5 | 33 |
| 15 | bis-MECCA | 0.5 | 37 |
| 16 | bis-CCA** | 0.5 | 12 |
| 17 | bis-CCA | 0.5 | 15 |
| 18 | bis-CCA | 0.5 | 17 |

*bis-MECCA is 1,6-diaminohexane-N,N'-bis(2-cyano-3-[4-methoxyphenyl] propenamide), a cinnamamide of the prior art
**bis-CCA is 1,6-diaminohexane-N,N'-bis(2-cyano-3-phenylpropenamide), a cinnamamide of the prior art.

The results show that the cinnamamides of the invention are significantly less volatile than those of the prior art.

EXAMPLE 7

The effects of the cinnamamides of the invention on the quality of nylon film was evaluated. Films having a thickness of 1 mil were prepared in a manner analogous to that disclosed in Example 3 above using each of Tinuvin 327 (T-327), Tinuvin 234 (T-234) (Tinuvin is a trademark of the Ciba-Geigy Corporation), CAmX and CAHM at 1 wt % loadings. The quality of the films was judged on % haze (ASTM D1003), 20° gloss (ASTM D2457), a visual rating of dirt/gels, and yellowness index ASTM D1925, MacBeth CI-3100). The results are shown in Table 2 below.

TABLE 2

Comparison of the quality of Nylon 6 Films containing β-phenyl substituted cinnamamide dimers and commercial benzotriazole UV absorbers.

| | | Haze % | | 20° Gloss | | | Yellow- |
|---|---|---|---|---|---|---|---|
| Sample # | Additive | High | Low | High | Low | Dirt/Gels | ness |
| 19 | Control | 1.0 | 0.8 | 190.7 | 174.2 | 1–12 | 1.761 |
| 20 | CAmX | 1.8 | 1.3 | 187.3 | 179.3 | 1–23 | 1.700 |
| 21 | CAHM | 1.5 | 1.4 | 184.4 | 176.6 | 1–16 | 1.816 |
| 22 | T-327 | 1.3 | 1.1 | 187.8 | 181.7 | 1–14 | 1.908 |
| 23 | T-234 | 1.0 | 0.7 | 188.4 | 186.2 | 0–13 | 1.944 |

The results show that the cinnamamides of the invention perform comparably to (or better than—yellowness) commercially available stabilizers.

EXAMPLE 8

The effects of the cinnamamides of the invention on the quality of polyester film was evaluated. Polyester [poly(ethyleneterephthlate), PET] films having a thickness of 1 mil were prepared in a manner analogous to that disclosed in Example 6 above using each of Uvinul 3050 (U-3050), (HBP) Uvinul 4050H (U-4050), (HALS) (Uvinul is a trademark of BASF Corporation), Mixxim BB-200 (BB-200) (BZT) (Mixxim is a trademark of Fairmount Chemical Co., Inc.), CAmX, and CAHM at 1 wt. % loadings. The films were judged based on a visual inspection of clarity (good, fair, poor), and on yellowness index (ASTM D1925, Macbeth CI 3100). The results are shown in Table 3 below.

TABLE 3

Comparison of PET films containing β-phenyl substituted cinnamamide dimers and commercial hydroxybenzophenone, benzotriazole, and HALS light stabilizers.

| Sample # | Additive | Clarity | Yellowness |
|---|---|---|---|
| 24 | Control | Good | 0.998 |
| 25 | CAmX | Good | 1.077 |
| 26 | CAHM | Fair | 1.462 |
| 27 | U-4050 | Fair | 1.205 |
| 28 | U-3050 | Fair | 1.605 |
| 29 | BB-200 | Good | 1.353 |

The results show that the cinnamamides of the invention perform comparably to (or better than—yellowness) commercially available stabilizers.

EXAMPLE 9

The photostability of the cinnamamides of the invention was evaluated. Each of CAmX, CAHM, Tinuvin P(BZT), and methyl cinnamate (MC) and poly(methylmethacrylate) (PMMA) was dissolved in dimethylformamide (DMF) and spin-coated on 1 inch quartz optical windows using a Headway Research Model 1-EC101D-R435 spin coater at speeds between 3500 and 7500 rpm. The proportions at which each component was combined and the spin coater speeds are reported in Table 4 below. The resulting films were cured at 95° C. for 15 minutes. The concentration of the additive in the polymer was adjusted such that the absorbencies of the maxima near 300 nm were between 0.47 and 0.60. The samples were irradiated in an Atlas SuncChex Fadeometer with a 280 nm filter and run at an irradiance of 0.55 W/m² and a temperature of 63° C. Data points were taken at 0, 8, 40, and 88 hours of irradiance. The data are presented as the percent of optical density (OD) remaining at the maximum for each additive relative to the optical density at the same wavelength before irradiation. The results are shown in Table 5 below.

TABLE 4

Compositions and spin coater speed utilized for the preparation of PMMA films of β-substituted cinnamamides and commercial stabilizers.

| Additive (g) | PMMA (g) | DMF (g) | Spin Speed (rpm) |
|---|---|---|---|
| CAmX 0.039 | 0.742 | 2.0 | 3500 |
| CAHM 0.035 | 0.742 | 2.0 | 3500 |
| MC 0.01 | 0.390 | 1.43 | 7500 |
| Tinuvin P ® 0.0095 | 0.340 | 0.96 | 3500 |

TABLE 5

Comparison of the permanence of β-phenyl substituted cinnamamide dimers, methyl cinnamate and a commercial benzotriazole upon irradiation in PMMA film

| | | | OD Remaining After Irradiation (%) | | |
|---|---|---|---|---|---|
| Sample # | Additive | Initial OD | 8 h | 40 h | 88 h |
| 30 | MC | 0.599 | 65 | 52 | 41 |
| 31 | CAmX | 0.561 | 97 | 63 | 88 |
| 32 | CAHM | 0.481 | 99 | 96 | 93 |
| 33 | Tinuvin P | 0.584 | 100 | 99 | 98 |

The results show that the cinnamamides of the invention perform equivalently to commercially available stabilizers.

EXAMPLE 10

The effectiveness of the cinnamamides of the invention as UV absorbers for polyester fiber was evaluated. Each of the additives reported in Table 6 below was tumble blended with dry AlliedSignal commercially available polyester [poly(ethyleneterephthalate), (PET)] at loadings of 0.25, 0.5 and 1.0 wt. %. These mixtures were compounded on a twin screw extruder, with a melt temperature of 290° C. and a residence time of approximately one minute, into approximately ⅛" filament and pelletized after cooling using standard equipment. The compounded material was dried for 16 hours under vacuum at 160° C. This material was spun into fiber by extruding the polymer at a spinning temperature of 290° C. into 32 filaments through a spinnerette with orifices 0.081" long and 0.024" wide at a throughput of 7.8 lbs/hour. The undrawn filaments were solidified in an air quench column and taken up at winder speeds of 276 m/minute. The undrawn fiber was drawn in one stage using conventional heated rolls and a hot shoe. The temperature of the first roll was 100° C. and that of the second roll and the hot shoe positioned between the rolls was 200° C. The take up speed was 183 m/minute resulting in a draw ratio of 5.7.

The breaking strength retention (BSR) of the fibers prepared via the above described process was determined according to 49CFR Ch. V (10/1/86) Federal Motor Vehicle Standard No. 209 procedures. BSR values reported in Table 5 are the average of five measurements. The BSR of the fibers was determined after 112, 150, 225, and 450 kJ/m² doses in the SAE J1885 test.

TABLE 6

Comparison of fiber BSR following UV irradiation (SAE J1885) of PET fiber containing β-phenyl substituted cinnamamide dimers and commercial benzotriazole UV absorbers.

| Sample # | Sample | Breaking Strength Retention (BSR) % | | | |
|---|---|---|---|---|---|
| | | 112 kJ/m$^2$ | 150 kJ/m$^2$ | 225 kJ/m$^2$ | 450 kJ/m$^2$ |
| 34 | Control | nd** | 44.33 | 30.9 | 16.5 |
| 35 | 1.0 wt. % CAHM | nd | 51.1 | 52.2 | 36.7 |
| 36 | 1.0 wt. % CAmX | nd | 45.6 | 44.4 | 27.8 |
| 37 | 0.25 wt. % T-234* | 50.0 | nd | 39.6 | 24.8 |
| 38 | 0.5 wt. % T-234 | 50.0 | nd | 38.1 | 21.1 |
| 39 | 1.0 wt. % T-234 | 55.8 | nd | 41.4 | 27.9 |
| 40 | 0.25 wt. % T-840* | 47.9 | nd | 32.4 | 20.7 |
| 41 | 0.5 wt. % T-840 | 57.1 | nd | 34.1 | 23.2 |
| 42 | 1.0 wt. % T-840 | 58.7 | nd | 36.5 | 26.4 |

*T-234 is Tinuvin 234 and T-840 is Tinuvin 840 (Tinuvin is a trademark of the Ciba-Geigy Corporation)
**nd = not determined.

The results show that the cinnamamides of the invention outperform or perform equivalently to commercially available stabilizers.

EXAMPLE 11

The effect of the each of the additives listed in Table 7 below on the fade resistance of fabrics was tested in standard seat belt webbing woven from fiber produced in accordance with the method reported in U.S. Pat. No. 4,349,501 which is hereby incorporated by reference. The polyester [poly (ethyleneterephthalate), PET] resin was comprised of a pellet blend of virgin resin and an appropriate quantity of 5% masterbatch required to achieve the desired loading in the final product. The masterbatches were formed in a manner consistent with that described for the production of the compounded materials in Example 10. Polyester [poly (ethyleneterephthalate), PET] narrow webbing woven to match the standard North American seat belt webbing specifications were used in all fabric fade resistance trials. The webbing construction consisted of 342 warp ends of 1300 denier zero twist fiber having a 100 filament count with a filling yarn of either 500 or 840 denier (most typically 840 denier) zero twist polyester woven at 17.6 picks per inch, a pick being an insertion and return. The knitted locking stitch was formed of 500 denier, 70 filament, zero twist polyester fiber. All webbing was woven on a Mueller needle loom, model ND, to be nominally 2" in width with a thickness of 0.047". All seat belt webbing met the requirements of the Federal Motor Vehicle Standard No. 209 (FMVSS 209) in addition to General Motors Engineering Standards Specification GM2704M. Standard disperse dye solutions were padded on greige PET seat belt webbing. The dye was applied from a dye bath via a single dip/single squeeze process and the webbing was then passed through an air convection predrier at a temperature of 150° F. (71° C.) with a nominal residence time of two minutes on a commercial Benz thermosol range. The dye and coated web was then passed through a rubber pinch braking roller and into an electric air convection thermosol oven heated at 215° C. at a speed of 1 yd/min to complete the dyeing of the web. The webbing residence time in the thermosol oven was between 1.5–2.0 min. The dyed web was then neutralized in a clearing bath of 2 g/L caustic soda and 2 g/L sodium hydrosulfite at 81° F. (27° C.), washed with detergent in two separate baths at 205°–212° F. (96°–100° C.), rinsed with hot water at 205°–212° F. (96°–100° C.) and then rinsed in a cold solution of 5 g/L acetic acid (pH 4.5–5.0). The webbing was then dried by passing over two steam cans and was taken up for UV testing of dye lightfastness, and breaking strength retention (BSR) using the SAE J1885 test method. Delta E measurements were carried out according to CIE Lab specifications using a Hunter calorimeter. The results are reported in Table 7 below.

TABLE 7

Comparison of fade resistance (ΔE) and BSR results for seatbelt webbing containing β-phenyl substituted cinnamamide dimers and commercial benzotriazole UV absorbers.

| | | | Dose (kJ/m$^2$) | | | | |
|---|---|---|---|---|---|---|---|
| | | | 150 | 225 | | 488 | |
| Sample # | Sample | Color | ΔE | ΔE | BSR % | ΔE | BSR % |
| 43 | Control | Red | 2.8 | 3.8 | 77 | 6.7 | 72 |
| 44 | 0.5% T-234* | Red | 2.2 | 4.0 | 81 | 6.3 | 76 |
| 45 | 1.0% T-234 | Red | 2.3 | 3.6 | 78 | 6.1 | 75 |
| 46 | 0.5% BB-200* | Red | 2.2 | 3.0 | 82 | 5.2 | 78 |
| 47 | 1.0% CAHM | Red | 2.4 | 3.3 | 76 | 7.1 | 72 |
| 48 | 1.0% CAmX | Red | 2.6 | 4.0 | 80 | 6.6 | 75 |
| 49 | Control | Tan | 2.0 | 3.2 | 72 | 5.6 | 61 |
| 50 | 0.5% T-234 | Tan | 1.6 | 1.8 | 78 | 4.0 | 72 |
| 51 | 1.0% T-234 | Tan | 1.3 | 1.5 | 80 | 3.2 | 74 |
| 52 | 0.5% BB-200 | Tan | 0.9 | 1.3 | 82 | 2.7 | 78 |
| 53 | 1.0% CAHM | Tan | 1.9 | 2.3 | 78 | 4.2 | 72 |
| 54 | 1.0% CAmX | Tan | 1.2 | 1.9 | 81 | 4.3 | 76 |
| 55 | Control | Gray | 1.2 | 2.1 | 76 | 4.4 | 70 |
| 56 | 0.5% T-234 | Gray | 1.0 | 1.4 | 82 | 3.3 | 75 |
| 57 | 1.0% T-234 | Gray | 0.8 | 1.0 | 83 | 2.1 | 77 |
| 58 | 0.5% BB-200 | Gray | 1.1 | 1.0 | 82 | 1.8 | 81 |
| 59 | 1.0% CAHM | Gray | 1.1 | 2.1 | 80 | 4.1 | 74 |
| 60 | 1.0% CAmX | Gray | 1.1 | 1.7 | 83 | 3.8 | 77 |

*T-234 represents Tinuvin 234 and BB-200 represents Mixxim BB-200.

The results show that cinnamamides of the invention improve webbing breaking strength relative to controls and perform comparably to commercially available stabilizers.

We claim:

1. A composition comprising at least one compound of the formula:

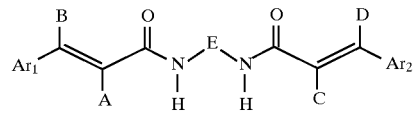

wherein
(i) Ar$_1$ and Ar$_2$ are the same or different and are selected from the group consisting of phenyl, heterocyclicaromatic, annelated phenyl and annelated heterocyclicaromatic groups and may be substituted in any position with the same or different group(s);
(ii) B and D are the same or different organic groups but neither is hydrogen;
(iii) A and C are the same or different organic groups; and
(iv) E is a divalent or trivalent organic group excluding compounds, including isomers thereof, wherein Ar$_1$ and Ar$_2$ are the same and are phenyl and are substituted with —OR wherein R is hydrogen or an organic group, A and C are the same and are cyano, B and D are the same and are alkyl or alkenyl of 1–35 carbon atoms and E is a divalent organic group; except when such compounds are combined with other compounds of said formula which do not have this excluded structure.

2. A composition comprising at least one compound of the formula:

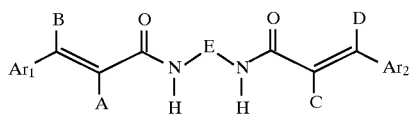

wherein:
(i) $Ar_1$ and $Ar_2$ are the same or different and are selected from the group consisting of phenyl, heterocyclicaromatic, annelated phenyl, and annelated heterocyclicaromatic radicals and may be substituted in any position with the same or different groups;
(ii) B and D are the same or different organic radicals but neither is hydrogen;
(iii) A and C are the same or different and are selected from the group consisting of cyano, ester ($CO_2R$) wherein R is any organic group, and amide (CONHR) wherein R is hydrogen or any organic group and
(iv) E is a divalent or trivalent organic radical excluding compounds, including isomers thereof, wherein: $Ar_1$ and $Ar_2$ are the same and are phenyl and are substituted with —OR wherein R is hydrogen or an organic group, A and C are the same and are cyano, B and D are the same and are alkyl or alkenyl of 1–35 carbon atoms and E is a divalent organic group; except when they are used in combination with other compounds of said formula which do not have this excluded structure.

3. A composition comprising a compound of the formula:

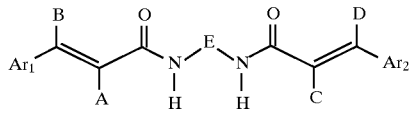

wherein:
(i) $Ar_1$ and $Ar_2$ are-the same or different and are selected from the group consisting of phenyl, heterocyclicaromatic, annelated phenyl and annelated heterocyclicaromatic groups which may be substituted in any position with the same or different group(s) selected from the group consisting of: substituted or unsubstituted straight-chain or branched alkyl of from 1 to ca. 25 carbon atoms wherein when said alkyl is substituted, it is substituted with a group selected from the group consisting of cyano, alkoxy, halo, amino and silyl; unsubstituted or substituted straight-chain or branched alkenyl of from 2 to ca. 25 carbon atoms wherein when said alkenyl is substituted, it is substituted with a group selected from the group consisting of cyano, alkoxy, halo, amino and silyl; cyano; nitro; halo; thioether; alkyl or arylsulfone; sulfonic ester; acetal, cyclic acetal; ketal, cyclic ketal; phenyl, substituted phenyl, multiply substituted phenyls wherein said phenyls may be substituted with any of the groups listed above; biphenyl, substituted biphenyl; pyridyl, substituted pyridyl and heterocyclicaromatics; and —OR where R is hydrogen or any organic group;
(ii) B and D are the same or different organic radicals but neither is hydrogen and are selected from the group consisting of substituted or unsubstituted straight-chain or branched alkyl of from 1 to ca. 25 carbon atoms wherein when said alkyl is substituted, it is substituted with a group selected from the group consisting of cyano, alkoxy, halo, amino and silyl; substituted or unsubstituted straight-chain or branched alkenyl of from 3 to ca. 25 carbon atoms wherein the double bonds are not in conjugation with the cinnamamide chromophore double bond and wherein when said alkenyl is substituted, it is substituted with a group selected from the group consisting of cyano, alkoxy, halo, amino and silyl; cyano; nitro; halo; thioether; alkyl or arylsulfone; sulfonic ester; acetal, cyclic acetal; ketal, cyclic ketal; phenyl, substituted phenyl, multiply substituted phenyls wherein said phenyls may be substituted with any of the groups listed above; biphenyl, substituted biphenyl; pyridyl, substituted pyridyl and heterocyclicaromatics; and —OR where R is hydrogen or any organic group;
(iii) A and C are the same or different and are selected from the group consisting of cyano, ester ($CO_2R$) wherein R may be any organic group, and amide (CONHR) wherein R may be hydrogen or any organic group; and
(iv) E is a divalent or trivalent organic groups excluding compounds, including isomers thereof, wherein: $Ar_1$ and $Ar_2$ are the same and are phenyl and are substituted with —OR wherein R is hydrogen or an organic radical, A and C are the same and are cyano, B and D are the same and are alkyl or alkenyl of 1–35 carbon atoms and E is a divalent organic radical; except when said compounds are combined with other compounds of said formula which do not have this excluded structure.

4. A composition comprising a compound of the formula:

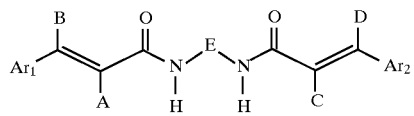

wherein
(i) $Ar_1$ and $Ar_2$ are the same or different and are selected from the group consisting of phenyl, heterocyclicaromatic, annelated phenyl, and annelated heterocyclicaromatic groups and may be substituted in any position with the same or different groups;
(ii) B and D are the same or different organic groups but neither is hydrogen;
(iii) A and C are the same or different and are selected from the group consisting of cyano, ester ($CO_2R$) wherein R is any organic group, and amide (CONHR) wherein R is hydrogen or any organic group; and
(iv) E is a divalent or trivalent organic group providing that $Ar_1$, $Ar_2$, B and D are not —OR substituted.

5. A composition comprising a compound of the formula:

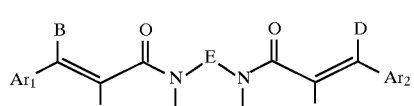

wherein
(i) $Ar_1$, $Ar_2$, B and D are the same or different phenyl groups and may be substituted in any position with the same or different group(s) selected from the group consisting of: substituted or unsubstituted straight chain or branched alkyl of from 1 to ca. 25 carbon atoms wherein when said alkyl is substituted, it is substituted with a group selected from the group consisting of cyano, alkoxy, halo, amino and silyl; unsubstituted or substituted straight chain or branched alkenyl of from 2 to ca. 25 carbon atoms wherein when said alkenyl is substituted, it is substituted with a group selected from the group consisting of cyano, alkoxy, halo, amino and silyl; cyano; nitro; halo; thioether; alkyl or arylsulfone; sulfonic ester; acetal, cyclic acetal; ketal, cyclic ketal; phenyl, substituted phenyl, multiply substituted phenyls wherein said phenyls may be substituted with any of the groups listed above; biphenyl, substituted biphenyl; pyridyl, substituted pyridyl and heterocyclicaromatics; and —OR where R is hydrogen or any organic group;

(ii) A and C are the same or different and are selected from the group consisting of cyano, ester ($CO_2R$) wherein R is any organic group, and amide (CONHR) wherein R is hydrogen or any organic group; and (iii) E is a divalent organic radical selected from the group consisting of substituted and unsubstituted straight or branched chain aliphatic radicals of from 2 to ca. 20 carbon atoms; substituted or unsubstituted aromatic or heterocyclic aromatic radicals, siloxane or polysiloxane containing divalent radicals of the structure R'—O$(Si(R)_2O)_n$—R' wherein R and R' are substituted or unsubstituted straight chain or branched alkyl or aromatic groups of from 1 to ca. 20 carbon atoms excluding compounds, including isomers thereof, wherein: $Ar_1$ and $Ar_2$ are the same and are phenyl and are substituted with —OR wherein R is hydrogen or an organic radical, A and C are the same and are cyano, B and D are the same and are alkyl or alkenyl of 1–35 carbon atoms and E is a divalent organic radical; except when said compounds are used in combination with other compounds of said formula which do not have this excluded structure.

6. A composition comprising a compound of the formula:

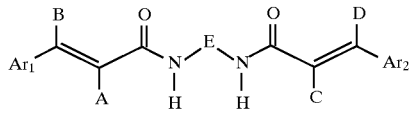

wherein
(i) $Ar_1$, $Ar_2$, B and D are each unsubstituted phenyl;
(ii) A and C are each cyano; and
(iii) E is a divalent organic group selected from the group consisting of substituted and unsubstituted straight or branched chain aliphatic radicals of from 2 to ca. 20 carbon atoms; substituted or unsubstituted aromatic or heterocyclic aromatic groups, siloxane or polysiloxane containing di valent groups of the structure R'—O$(Si(R)_2O)_n$—R' wherein R and R' are substituted or unsubstituted straight chain or branched alkyl or aromatic groups of from 1 to ca. 20 carbon atoms.

7. A composition comprising a compound of the formula:

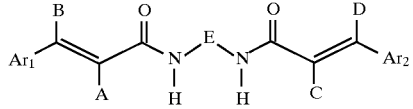

wherein
(i) $Ar_1$, $Ar_2$, B and D are each unsubstituted phenyl;
(ii) A and C are each cyano; and
(iii) E is —$(CH_2)_6$—.

8. A composition comprising a compound of the formula:

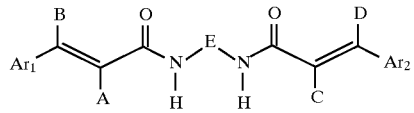

wherein
(i) $Ar_1$, $Ar_2$, B and D are each unsubstituted phenyl;
(ii) A and C are each cyano; and
(iii) E is 2,4-toluenediyl.

9. A composition comprising a compound of the formula:

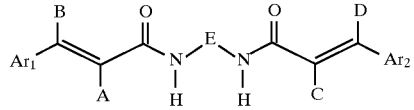

wherein
(i) $Ar_1$, $Ar_2$, B and D are each unsubstituted phenyl;
(ii) A and C are each cyano; and
(iii) E is 3,4-toluenediyl.

10. A composition comprising a compound of the formula:

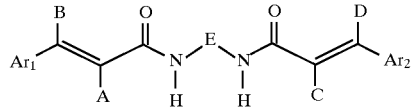

wherein
(i) $Ar_1$, $Ar_2$, B and D are each unsubstituted phenyl;
(ii) A and C are each cyano; and
(iii) E is m-xylylenediyl.

11. A composition comprising a compound of the formula:

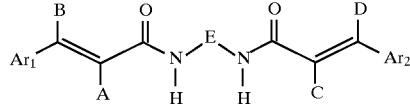

wherein
$Ar_1$, $Ar_2$, B and D are each unsubstituted phenyl;
A and C are each cyano; and
E is 4,4-octafluorobiphenyldiyl.

12. A composition comprising a compound of the formula:

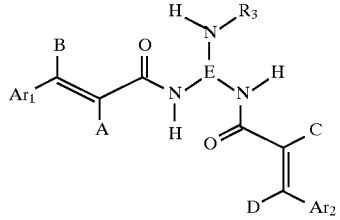

wherein
(i) $Ar_1$, $Ar_2$, B and D are each unsubstituted phenyl;
(ii) A and C are each cyano;
(iii) E is 2,4,6-melaminetriyl; and (iv) R$_3$ is any organic group.

13. The composition of claim 2 wherein said composition comprises at least two compounds of said formula.

14. The composition of claim 3 wherein said composition comprises at least two compounds of said formula.

15. The composition of claim 4 wherein said composition comprises at least two compounds of said formula.

16. The composition of claim 5 wherein said composition comprises at least two compounds of said formula.

17. The composition of claim 6 wherein said composition comprises at least two compounds of said formula.

18. The composition of claim 17 wherein said composition comprises at least two compounds selected from the group consisting of

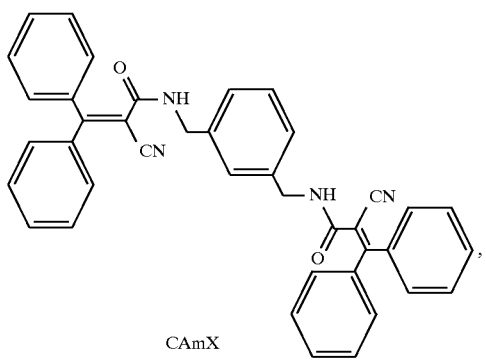

CAmX

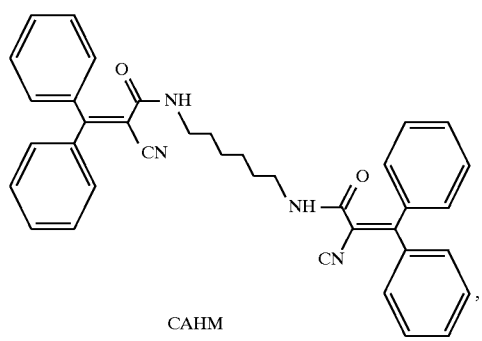

CAHM

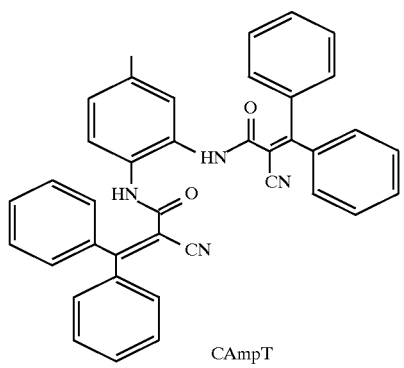

CAmpT and

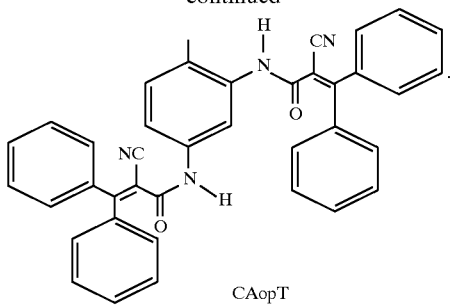

CAopT

19. The composition of claim 2 wherein said composition additionally contains at least one compound selected from the group consisting of hindered amines, phosphites, phenolic antioxidants, thioethers, metal dithiolates, sulfoxides, benzotriazoles, hydroxybenzophenones, cinnamates, benzylidene malonates, nickel chelates, oxanilides and copper-based heat stabilizers.

20. The composition of claim 3 wherein said composition additionally contains at least one compound selected from the group consisting of hindered amines, phosphites, phenolic antioxidants, thioethers, metal dithiolates, sulfoxides, benzotriazoles, hydroxybenzophenones, cinnamates, benzylidene malonates and nickel chelates, oxanilides and copper-based heat stabilizers.

21. The composition of 4 wherein said composition additionally contains at least one compound selected from the group consisting of hindered amines, phosphites, phenolic antioxidants, thioethers, metal dithiolates, sulfoxides, benzotriazoles, hydroxybenzophenones, cinnamates, benzylidene malonates and nickel chelates, oxanilides and copper-based heat stabilizers.

22. The composition of claim 5 wherein said composition additionally contains at least one compound selected from the group consisting of hindered amines, phosphites, phenolic antioxidants, thioethers, metal dithiolates, sulfoxides, benzotriazoles, hydroxybenzophenones, cinnamates, benzylidene malonates and nickel chelates, oxanilides and copper-based heat stabilizers.

23. The composition of claim 6 wherein said composition additionally contains at least one compound selected from the group consisting of hindered amines, phosphites, phenolic antioxidants, thioethers, metal dithiolates, sulfoxides, benzotriazoles, hydroxybenzophenones, cinnamates, benzylidene malonates and nickel chelates, oxanilides and copper-based heat stabilizers.

24. A composition comprising at least one compound of the formula

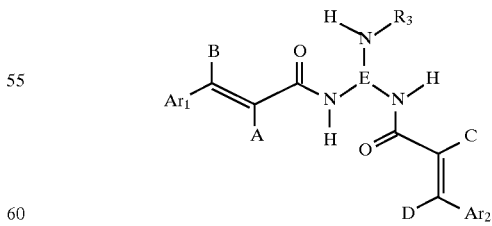

wherein:

(i) Ar$_1$ and Ar$_2$ are the same or diferent and are selected from the group consisting of phenyl, heterocyclicaromatic, annelated phenyl and annelated heterocyclicaromatic radicals and may be substituted in any position with the same or different group(s);

(ii) B and D are the same or different organic radicals but neither is hydrogen;

(iii) A and C are the same or different organic group; and (iv) E is a trivalent organic group; and (v) R$_3$ is any organic group.

25. A sunscreen formulation comprising a compound of claim 3.

26. A compound defined by the formula

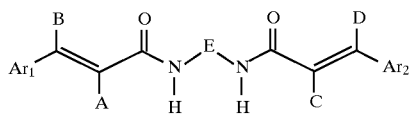

wherein (i) Ar$_1$ and Ar$_2$ are the same or different and are selected from the group consisting of phenyl, heterocyclicaromatic, annelated phenyl and annelated heterocyclicaromatic radicals and may be substituted in any position with the same or different groups(s);

(ii) B and D are the same or different organic radicals but neither is hydrogen;

(iii) A and C are the same or different organic radicals; and (iv) E is a divalent or trivalent organic radical excluding compounds, including isomers thereof, wherein Ar$_1$ and Ar$_2$ are the same and are phenyl and are substituted with —OR wherein R is hydrogen or an organic radical, A and C are the same and are cyano, B and D are the same and are alkyl or alkenyl of 1–35 carbon atoms and E is a divalent radical.

27. A compound as recited by claim 26, wherein:

(i) Ar$_1$ and Ar$_2$ are the same or different and are selected from the group consisting of phenyl, heterocyclicaromatic, annelated phenyl and annelated heterocyclicaromatic radicals and may be substituted in any position with the same or different groups(s);

(ii) B and D are the same or different organic radicals but neither is hydrogen;

(iii) A and C are the same or different and are selected from the group consisting of cyano, ester (CO$_2$R), wherein R is any organic radical, and amide (CONHR), wherein R is hydrogen or any organic radical; and (iv) E is a divalent or trivalent organic radical excluding compounds, including isomers thereof, wherein Ar$_1$ and Ar$_2$ are the same and are phenyl and are substituted with —OR wherein R is hydrogen or an organic radical, A and C are the same and are cyano, B and D are the same and are alkyl or alkenyl of 1–35 carbon atoms and E is a divalent radical.

28. A compound as recited by claim 26, wherein:

(i) Ar$_1$ and Ar$_2$ are the same or different and are selected from the group consisting of phenyl, heterocyclicaromatic, annelated phenyl and annelated heterocyclocaromatic radicals which may be substituted in any position with the same or different group(s) selected from the group consisting of: substituted or unsubstituted straight-chain or branched alkyl of from 1 to ca. 25 carbon atoms wherein when said alkyl is substituted, it is substituted with a group selected from the group consisting of cyano, alkoxy, halo, amino and silyl; unsubstituted or substituted straight-chain or branched alkenyl of from 2 to ca. 25 carbon atoms wherein straight-chain or branched alkenyl of from 2 to ca. 25 carbon atoms wherein when said alkenyl is substituted, it is substituted with a group selected from the group consisting of cyano, alkoxy, halo, amino, and silyl; cyano; nitro; halo; thioether; alkyl or arylsulfone; sulfonic ester; acctal cyclic acetal; ketal, cyclic ketal; phenyl, substituted phenyl, multiple substituted phenyls wherein said phenyls may be substituted with any of the groups listed above; biphenyl, substituted biphenyl; pyridyl; substituted pyridyl and heterocyclicaromatics; and —OR where R is hydrogen or any organic radical;

(ii) B and D are the same or different organic radicals but neither is hydrogen and are selected from the group consisting of substituted or unsubstituted straight-chain or branched alkyl of from 1 to ca. 25 carbon atoms wherein when said alkyl is substituted, it is substituted with a group selected from the group consisting of cyano, alkoxy, halo, amino and silyl; substituted or unsubstituted-straight-chain or branched alkenyl of from 3 to ca. 25 carbon atoms wherein the double bonds are not in conjunction with the cinnamamide chromophore double bond and wherein when said alkenyl is substituted, it is substituted with a group selected from the group consisting of cyano, alkoxy, halo, amino and silyl; cyano, nitro, halo, thioether; alkyl or arylsulfone; sulfonic ester; acetal, cyclic acetal; ketal, cyclic ketal; phenyl, substituted phenyl, multiple substituted phenyls wherein said phenyls may be substituted with any of the groups listed above; biphenyl, substituted biphenyl, pyridyl, substituted pyridyl and heterocyclicaromatics; and —OR where R is hydrogen or any organic radical;

(iii) A and C are the same or different and are selected from the group consisting of cyano, ester (CO$_2$R) wherein R is any organic radical, and amide (CONHR) wherein R is hydrogen or any organic radical; and (iv) E is a divalent or trivalent organic radical excluding compounds, including isomers thereof, wherein Ar$_1$ and Ar$_2$ are the same and are phenyl and are substituted with —OR wherein R is hydrogen or an organic radical, A and C are the same and are cyano, B and D are the same and are alkyl or alkenyl of 1–35 carbon atoms and E is a divalent radical.

29. A compound as recited by claim 26, wherein:

(i) Ar$_1$ and Ar$_2$ are the same or different and are selected from the group consisting of phenyl, heterocyclicaromatic, annelated phenyl and annelated heterocyclocaromatic radicals and may be substituted in any position with the same or different groups(s);

(ii) B and D are the same or different organic radicals but neither is hydrogen;

(iii) A and C are the same or different and are selected from the group consisting of cyano, ester (CO$_2$R) wherein R is any organic radical, and amide (CONHR) wherein R is hydrogen or any organic radical; and (iv) E is a divalent or trivalent organic radical providing that Ar$_1$, Ar$_2$, B and D are not —OR substituted.

30. A compound as recited by claim 26, wherein:

(i) Ar$_1$, Ar$_2$, B and D are the same of different phenyl radicals and may be substituted in any position with the same or different group(s) selected from the group consisting of: substituted or unsubstituted straight-chain or branched alkyl of from 1 to ca. 25 carbon atoms wherein when said alkyl is substituted, it is substituted with a group selected from the group consisting of cyano, alkoxy, halo, amino and silyl; unsubstituted ot substituted straight-chain or branched alkenyl of from 2 to ca. 25 carbon atoms wherein straight-chain or branched alkenyl of from 2 to ca. 25 carbon atoms wherein when said alkenyl is substituted, it is substituted with a group selected from the group consisting of cyano, alkoxy, halo, amino, and silyl; cyano; nitro; halo; thioether; alkyl or arylsulfone; sulfonic ester; acetal, cyclic acetal; ketal, cyclic ketal; phenyl, substituted phenyl, multiple substituted phenyls wherein said phenyls may be substituted with any of the groups listed above; biphenyl, substituted biphenyl; pyridyl; substituted pyridyl and heterocyclicaromatics; and —OR where R is hydrogen or any organic radical;

(ii) A and C are the same or different and are selected from the group consisting of cyano, ester ($CO_2R$) wherein R is any organic radical, and amide ($CONHR$) wherein R is hydrogen or any organic radical; and (iii) E is a divalent or trivalent organic radical selected from the group consisting of substituted ot unsubstituted straight or branched chain aliphatic radicals of from 2 to ca. 20 carbon atoms; substituted or unsubstitued aromatic or heterocyclic aromatic radicals, siloxane or polysiloxane containing divalent radicals of the structure R'—$O(Si(R)_2O)_n$—R' wherein R and R' are substituted or unsubstituted straight chain or branched alkyl or aromatic radicals of from 1 to ca. 20 carbon atoms excluding compounds, including isomers thereof, wherein $Ar_1$ and $Ar_2$ are the same and are phenyl and are substituted with —OR wherein R is hydrogen or an organic radical, A and C are the same and are cyano, B and D are the same and are alkyl or alkenyl of 1–35 carbon atoms and E is a divalent radical.

31. A compound as recited by claim 26, wherein:

(i) $Ar_1$, $Ar_2$, B and D are each unsubstitued phenyl;

(ii) A and C are each cyano;

(iii) E is a divalent organic radical selected from the group consisting of substituted ot unsubstitued straight or branched chain aliphatic radicals of from 2 to ca. 20 carbon atoms; substituted or unsubstituted aromatic or heterocyclic aromatic radicals, siloxane or polysiloxane containing divalent radicals of the structure R'—$O(Si(R)_2O)_n$—R' wherein R and R' are substituted or unsubstituted straight chain or branched alkyl or aromatic radicals of from 1 to ca 20 carbon atoms.

32. A compound as recited by claim 26, wherein:

(i) $Ar_1$, $Ar_2$, B and D are each unsubstituted phenyl;

(ii) A and C are each cyano; and (iii) E is —$(CH_2)_6$—.

33. A compound as recited by claim 26, wherein:

(i) $Ar_1$, $Ar_2$, B and D are each unsubstituted phenyl;

(ii) A and C are each cyano; and (iii) E is 2,4-toluenediyl.

34. A compound as recited by claim 26, wherein:

(i) $Ar_1$, $Ar_2$, B and D are each unsubstituted phenyl;

(ii) A and C are each cyano; and (iii) E is 3,4-toluenediyl.

35. A compound as recited by claim 26, wherein;

(i) $Ar_1$, $Ar_2$, B and D are each unsubstituted phenyl;

(ii) A and C are each cyano; and (iii) E is m-xylylenediyl.

36. A compound as recited by claim 26, wherein:

(i) $Ar_1$, $Ar_2$, B and D are each unsubstituted phenyl;

(ii) A and C are each cyano; and (iii) E is 4, 4-octafluorobiphenyldiyl.

37. A compound as recited by claim 26, wherein:

(i) $Ar_1$, $Ar_2$, B and D are each unsubstitued phenyl;

(ii) A and C are each cyano;

(iii) E is 2,4,6melaminetriyl with a functional group having the formula $NHR_3$ attached thereto wherein $R_3$ is any organic radical.

38. A compound as recited by claim 26, wherein:

(i) $Ar_1$ and $Ar_2$ are the same or different and are selected from the group consisting of phenyl, heterocyclicaromatic, annelated phenyl and annelated heterocyclicaromatic radicals and may be substituted in any position with the same or different groups(s);

(ii) B and D are the same or different organic radicals but neither is hydrogen;

(iii) A and C are the same or different organic radicals; and (iv) E is a trivalent radical with a functional group having the formula $NHR_3$ attached thereto wherein $R_3$ is any organic radical.

* * * * *